United States Patent [19]

DeHarde et al.

[11] Patent Number: 5,312,372
[45] Date of Patent: * May 17, 1994

[54] SAFETY SYRINGE SYSTEM

[76] Inventors: Lawrence G. DeHarde, 2916 Davterive Dr.; Michael H. DeHarde, 2100 Montesquieu St., both of Chalmette, La. 70043

[*] Notice: The portion of the term of this patent subsequent to Jun. 10, 2010 has been disclaimed.

[21] Appl. No.: 61,702

[22] Filed: May 13, 1993

Related U.S. Application Data

[63] Continuation-in-part of Ser. No. 801,669, Dec. 2, 1991, Pat. No. 5,215,534.

[51] Int. Cl.⁵ .................................... A61M 5/32
[52] U.S. Cl. ................................... 604/198; 604/110
[58] Field of Search ............ 604/110, 118, 192, 196, 604/198, 197, 187, 117

[56] References Cited

U.S. PATENT DOCUMENTS

| | | | |
|---|---|---|---|
| 4,573,976 | 3/1986 | Sonpson et al. | 604/198 |
| 4,887,998 | 12/1989 | Martin et al. | 604/198 |
| 4,915,696 | 4/1990 | Frimer | 604/198 |
| 5,037,402 | 8/1991 | Bartman | 604/198 |
| 5,092,461 | 3/1992 | Adam | 604/198 |
| 5,215,534 | 6/1993 | De Horde et al. | 604/192 |

Primary Examiner—C. Fred Rosenbaum
Assistant Examiner—Manuel Mendez
Attorney, Agent, or Firm—Joseph T. Regard, Ltd.

[57] ABSTRACT

A safety system for use in conjunction with an instrument having a needle, wherein there is included a spring biased, locking pushbutton or activation tab apparatus which communicates with a locking safety sheath situated at the base of the hypodermic needle prior to activation. The safety sheath is in sliding, longitudinal communication about the needle, and is activated to its sheathing position by pressing a pushbutton or activation tab on the locking pushbutton or activation tab apparatus, directing the sheath from about the base of the needle to over the tip of the needle. Upon communication with the tip, the safety sheath deploys a locking hatch, preventing the urging of the sheath back to the base, and rendering the needle unreuseable. The present invention operates independently of the syringe plunger when utilized in conjunction with a syringe, allowing the drawing and injection of fluids without interference, and is sheathed in locking position upon urging of the pushbutton or activation tab, "clicking" the sheath into a locked position.

9 Claims, 7 Drawing Sheets

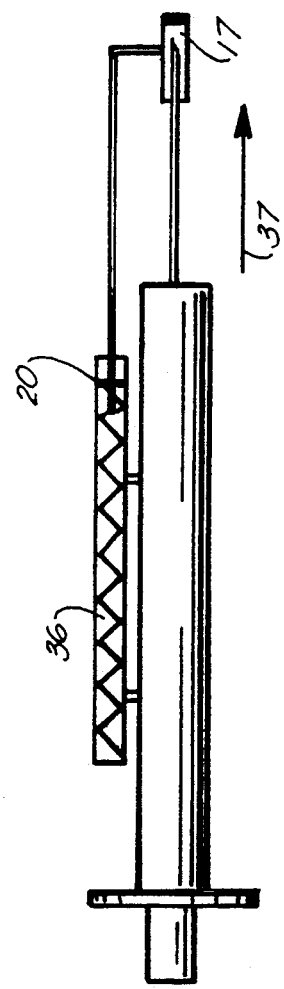
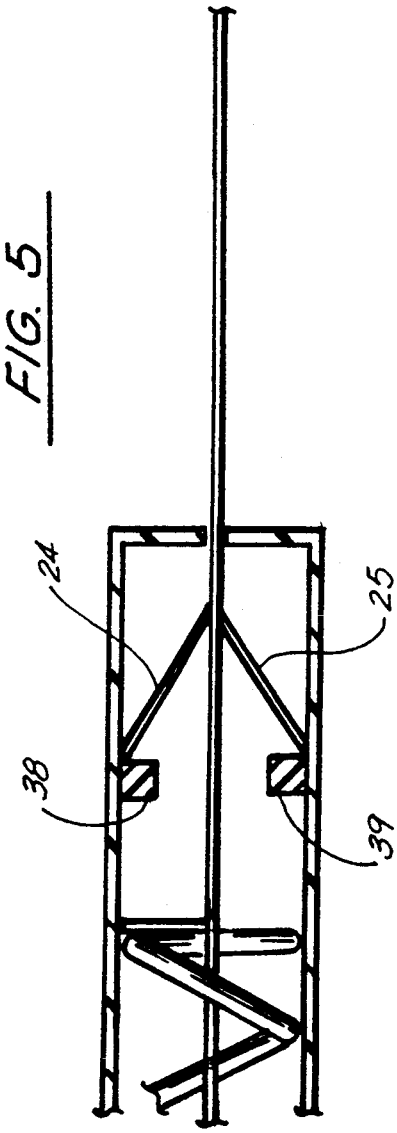

SAFETY SYRINGE SYSTEM

STATEMENT OF CONTINUING APPLICATION

The present invention is a continuation in part of U.S. patent application Ser. No. 07/801,669, now U.S. Pat. No. 5,215,534, filed Dec. 2, 1991 for a "Safety Syringe System", naming Lawrence and Michael DeHarde as inventors.

BACKGROUND OF INVENTION

1. Field of Invention

The present invention relates to apparatus for preventing infection from unsterile hypodermic needles or the like, and more particularly to a system for preventing needle stick or re-use of unsterile hypodermic needles or like items.

The present invention teaches in its preferred embodiment a hypodermic syringe wherein there is included a spring biased, locking pushbutton or activation tab apparatus exterior to the syringe plunger which communicates with a locking safety sheath situated at the base of the hypodermic needle prior to activation.

The safety sheath is in sliding, longitudinal communication about the needle, and is activated to its sheathing position by urging a pushbutton or activation tab on the locking pushbutton or activation tab structure in the direction of the needle, directing the sheath from about the base of the needle to over the tip of the needle. Upon communication with the tip, the safety sheath deploys a locking hatch, preventing the urging of the sheath back to the base, and rendering the needle thereafter un-reusable.

The locking apparatus of the present invention preferably operates independently of the syringe plunger, allowing the drawing and injection of fluids without interference, and is sheathed in locking position only upon the independent urging of the pushbutton or activation tab, "clicking" the sheath into a locked position.

2. Prior Art and General Background

While the prior art may teach a plurality of various devices configured to protect against needle sticks, none teach or contemplate the system as contemplated in the present invention, wherein there is provided redundant locking as a "fail-safe" apparatus.

Since the early 1980's it has been recognized that instruments which come into contact with human tissue fluids can comprise biohazards, particularly when those instruments come into contact with HIV, hepatitis, and other tissue infected with contagion.

Further, it has been recognized that the sharing and re-usage of disposable needles has transmitted HIV among intravenous drug users.

Consequently, there has evolved a plethora of redesigns of existing hypodermic syringes and related devices, wherein there has been incorporated features to prevent infection and, in the case of disposable systems, reuse.

Often, the distraction surrounding a medical emergency or like situation may result in used syringes not being identified as being particularly contaminated. This could result in the re-use of the syringe by a medical professional and potential contamination resulting therefrom.

Additionally, if the syringe is not properly disposed of an addict may thereafter utilize it to administer illegal drugs to himself and others, spreading the virus, bacteria, disease, or anything else which may be present on the point and shaft of the hollow metal needle.

It is for this reason that an easily operated, consistent and tamper proof, syringe needle capping system is needed, so that the utilized needle may be automatically capped immediately after use, even in the heat of a medical emergency, without distraction and in a consistent and unfailing manner.

A list of prior patents which may be of interest is presented below:

| U.S. Pat. No. | PATENTEE(S) | ISSUE DATE |
|---|---|---|
| 4,702,738 | | |
| 4,725,267 | Vaillancourt | 2/16/88 |
| 4,790,828 | Dombrowski et al | 12/13/88 |
| 4,804,371 | Vaillancourt | 2/14/89 |
| 4,813,940 | Parry | 3/21/89 |
| 4,838,863 | Allard et al | 6/13/89 |
| 4,486,796 | Carrell et al | 7/11/89 |
| 4,850,968 | Romano | 7/25/89 |
| 4,861,338 | Mathiesen et al | 8/29/89 |
| 4,863,434 | Bayless | 9/5/89 |
| 4,887,998 | Martin et al | 12/19/89 |
| 4,894,055 | Sudnak | 1/16/90 |
| 4,908,023 | Yuen | 3/13/90 |
| 4,921,486 | DeChellis et al | 5/01/90 |
| 4,932,940 | Walker et al | 6/12/90 |
| 4,936,830 | Verlier | 6/26/90 |
| 4,955,868 | Klein | 9/11/90 |
| 4,966,593 | Lennox | 10/30/90 |
| 4,986,818 | | |
| 4,994,046 | | |
| 5,026,353 | Bartman | 6/25/91 |

U.S. Pat. No. 4,702,738 addresses the problem of inadvertent pricks, but the safety is easily manipulated once the system is locked by manipulating the spring force, easily overcoming it by hand. Further, the difficulties in performing the basic functions of using the syringe are increased by the need for holding the shield handle during injection.

U.S. Pat. No. 4,725,267 addresses the problem of inadvertent pricks by covering the point of the needle, but activating it requires the operator to work in the area of the point of the needle, increasing the potential contamination risk simply to cover the needle. Further, the cover could be forced back exposing the needle, potentially causing a prick.

U.S. Pat. No. 4,790,828, issued in 1988, teaches a "Self-capping Needle Assembly", wherein in FIGS. 1, 2 and 6, there is contemplated a locking needle capping assembly utilizing biased blockage means, albeit distinguishable in operation and design from that contemplated by the present invention.

Namely, the activation system which must be manually lifted in the '828 system is more cumbersome to operate with one hand and could actually encourage needle stick, versus the present invention, which contemplates a push-button system wherein there is a lesser chance for needle stick during the activation of the capping mechanism.

U.S. Pat. No. 4,804,371 addresses the problem of inadvertent pricks by covering the needle, but can be pushed out of the way if one desires to overcome the system, thereby preventing re-use. U.S. Pat. No. 4,994,046, issued in 1991, discloses a "Needle Guard for Syringe", wherein there is taught a side mounted apparatus for controlling the shield means, albeit completely distinguishable in form and operation from the present invention.

U.S. Pat. No. 4,863,434, issued in 1989 describes an "automatic needle sheath for disposable syringe" wherein a needle capping assembly is disclosed (note FIG. "A") offering biased blocking members to cover the needle. However, the '434 patent fails to contemplate an efficient, inexpensive, and safe system as taught in the present invention.

U.S. Pat. No. 4,936,830 addresses the problem of inadvertent pricks and reuse, but works only on prefilled syringes.

U.S. Pat. No. 4,986,818, issued Jan. 22, 1991, and U.S. Pat. No. 4,990,141, issued Feb. 5, 1991, also teach single use syringes utilizing a type of safety capping assembly again distinguishable from the present invention, but nonetheless pertinent with respect to the generalized concept of a single use syringe system.

Finally, U.S. Pat. No. 5,026,353 issued Jun. 25, 1991 teaches a "multi-chamber safety syringe", contemplating a rather bulky, complicated, and expensive system for preventing needle stick, wherein there is taught essentially the incorporation of dual spring biased reciprocating pistons on opposing sides of the syringe to force forward a capping assembly.

As taught, the device of the '353 patent may not only be considered impractical, but also does not teach a safe locking mechanism over the needle. In fact, as the capping system is apparently contemplated, the cap is not locked in place over the needle and may in fact slide out of the needle cap, if the cap is urged towards the base of the needle, exposing it. Therefore, if one were to bump or sit atop the cap, the cap could slide back, sticking and potentially infecting that person.

GENERAL, SUMMARY DISCUSSION OF THE INVENTION

Although the prior discussed patents disclose a plethora of various needle capping systems, none teach or contemplate the reliable, inexpensive, and easily operated system of the present invention.

As may be discerned by a review of the above, one can understand why so few systems for preventing needle stick have been commercially successful in the marketplace.

Literally dozens of various apparatus configurations have been presented to prevent needle stick or syringe re-use, but all have their flaws, particularly with regard to ease of use, reliability, safety and cost.

The present system not only provides all of the above, but does so in a system which is less complicated than most of those contemplated in the prior art.

Unlike the prior art, the present invention provides a simple system for implementing a needle cap after use which is redundant, providing locking with regard to the needle cap once in the capping position, as well as a locking system in the initiating mechanism. This is done in an easy, push-button system designed to be literally fool proof and tamper proof.

The present invention contemplates in its preferred embodiment a plunger-type syringe and needle arrangement, with a side mounted, initiating mechanism in longitudinal communication with a capping or protective cover mechanism. Both the capping mechanism and protective cover incorporate oblique locking means for maintaining the system permanently in a locked, unsliding position once the locking pushbutton or activation tab has been initiated.

In the initiation mechanism, there is provided a spring biased pushbutton or activation tab and shaft arrangement, wherein the shaft moves longitudinally along its enveloping sleeve until it activates a one-way locking mechanism, while simultaneously biasing the protective cap along the needle until it covers the tip of the needle.

Once the needle tip has been covered, the one-way locking mechanism in both the initiation mechanism and protective cover engage, preventing any subsequent needle stick or re-use.

It is therefore an object of the present invention to provide a system for preventing needle stick which incorporates redundant protective cover locking means.

It is another object of the present invention to provide a system for preventing needle stick wherein there is included a side mounted, push-button initiation system incorporating a longitudinal migrating shaft and enveloping sheath for urging a protective cap along a needle, covering it.

It is another object of the present invention to provide a system for preventing needle stick, wherein there is implemented a protective sheath or cover for the needle which permanently locks in place once it slides over the tip of the needle. Lastly, it is an object of the present invention to provide a system for preventing needle stick or the like, which is inexpensive, reliable, and safe to implement and utilize.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 4 is a partially cut-away, side view of the embodiment of FIG. 1, illustrating in particular the initiation mechanism and needle cap or sheath after activation, and in the locked capping configuration.

FIG. 5 is a cut-away, enlarged view of the locking apparatus of the initiation mechanism of the embodiment of FIG. 1, illustrating the locking mechanism and system after activation, and in the locked configuration.

DETAILED DESCRIPTION OF THE PREFERRED, EXEMPLARY EMBODIMENT(S)

Figure 1:
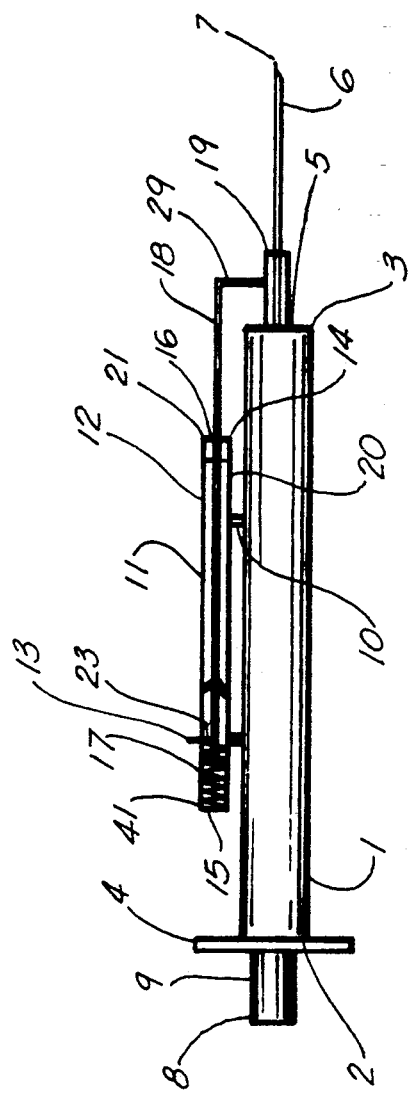
FIG. 1 is a side, partially cut-away view of the preferred embodiment of the safety syringe system of the present invention, illustrating its implementation in conjunction with a plunger syringe and needle.

As can be seen in FIG. 1, the safety syringe system of the preferred, exemplary embodiment of the present invention is designed to be implemented with an off-the-shelf plunger type syringe 1, wherein there is included a cylinder 12 having first (2) and second (3) ends and an outer wall 10, and finger tabs 4 for use in operation. Further included is a plunger 9, in sliding communication with the inner wall of the cylinder 11, the plunger having a push end 8.

Situated at the second end 3 of cylinder 11 is threaded needle connection means 5, to which a needle 6 having a needle point 7 is connected.

Figure 2:
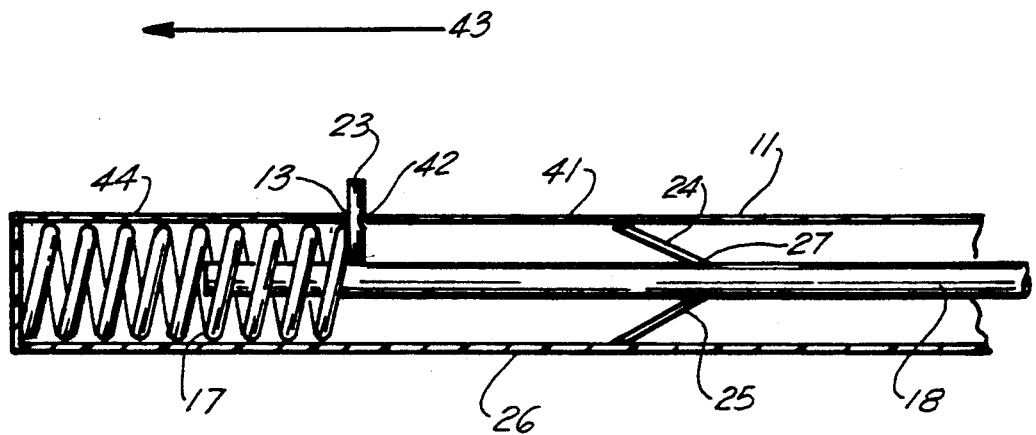
FIG. 2 is a cut-away, enlarged view of the pushbutton or activation tab area of the initiation mechanism of the embodiment of FIG. 1.

As illustrated in FIGS. 1 and 2, affixed to the lateral, outer side of the syringe body 10 is the locking initiation member 41, comprising a housing 11 having first (15) and second (14) ends, said housing 11 being configured to envelope the shaft 18 in alignment with the longitudinal axis of syringe 1.

Formed in housing 11 at the second end 14 is a shaft aperture 16, from which shaft 18 emanates. Formed on the outer edge of the housing 11, near the first end 15, is a plunger button aperture 13, out of which an activation button or tab 23 protrudes. The activation button or tab 23 is affixed at area 22 to the shaft 18 and is configured for applying lateral bias to the shaft relative to the housing, releasing the activation button or tab 23 from aperture, allowing the spring 17 to provide longitudinal force relative to the housing 11, forcing the shaft 18 generally toward the needle point 7. Activation button 23 further includes notch 42 provided in the outer wall of same for communication with housing 11, providing a means of locking the activation button or tab 23 in an uninitiated position, preventing accidental locking of the protective cover over the needle tip.

In the preferred embodiment of the present invention, notch 42 is cut at a right angle, so that in order to initiate activation button or tab 23, the user must apply longitudinal bias 43 to dislocate notch 42 from housing 11, and apply further, lateral pressure 44, fully releasing activation button or tab 23 from aperture 13, allowing shaft 18 to be guided by spring 17 bias in the direction needle tip.

Protruding at an oblique angle 27 from the side of the shaft 18 are locking members 24, 25, set at opposing sides of the shaft. The locking members 24, 25 are configured to communicate with the inner wall 26 of the housing 11 and to space the shaft 18 generally equidistant from the opposing inner side wall 26 of the housing.

Figure 3:
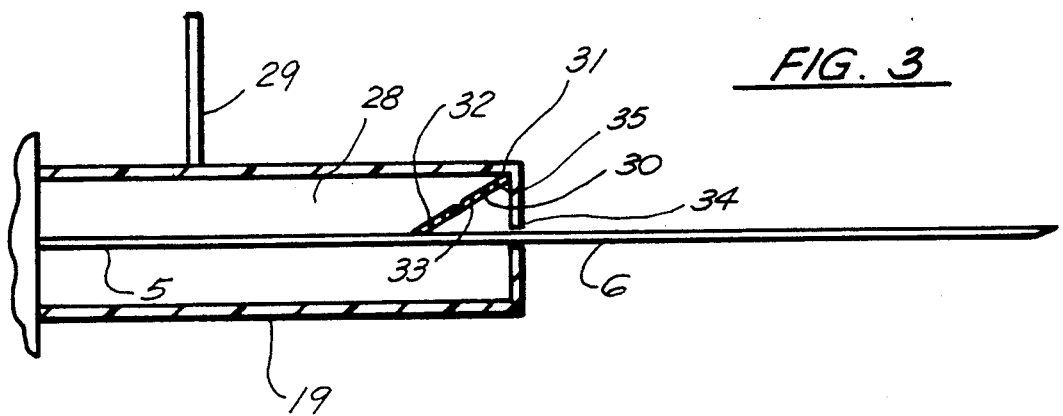
FIG. 3 is a cut-away, enlarged view of the needle cap or sheath of the embodiment of FIG. 1, illustrating the locking mechanism and system prior to activation.

As illustrated in FIGS. 1 and 3, communicating with shaft 18 via lateral shaft extension 29 is a protective cover 19 enveloping the needle 6 about its base, connection area 5, via cylindrical cavity 28, in the systems unprotected configuration, allowing needle 6 and point 7 to be exposed via the needle aperture 34.

A cap locking hatch 30 pliantly extends (note 31) at an oblique angle 35 from the inside wall of the protective cover 19 in communication with the needle 6 via conformed end 32. The cap locking hatch 30 has further formed therein needle tip notch 33, configured for receiving the needle tip or point 7 when the cap is in the closed position, as will be discussed infra.

As shown in FIGS. 2, 4 and 5, once the operator of the syringe has utilized it and wishes to make the syringe un-reusable, the operator merely presses the activation button or tab 23, releasing (note 36) spring 17, allowing it to thrust shaft 18, and thereby the protective cover 19, longitudinally 10 forward 37. This allows the locking members 24, 25 to pass between the first (38) and second (39) locking barriers or a locking ring, locking (note 20) the shaft permanently in the closed position, between barriers 38, 39 or locking the ring and the end wall of the housing 11, acting as a short stop 21.

Figure 6:
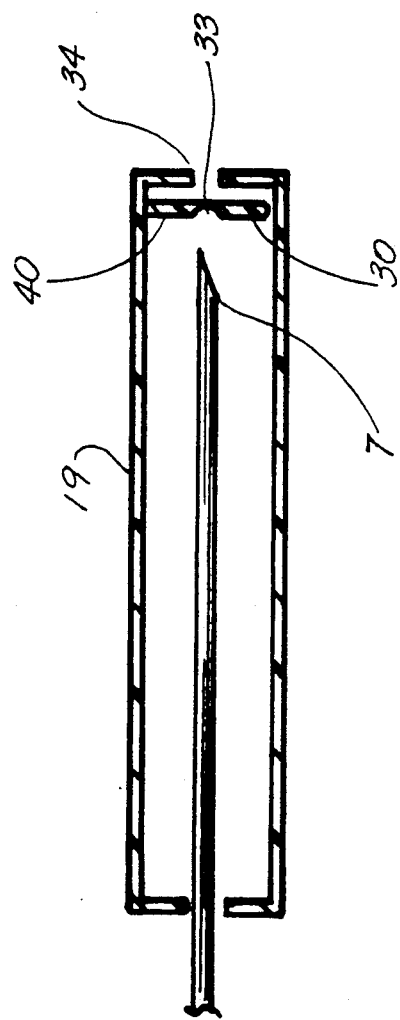
FIG. 6 is a cut-away, enlarged view of the locking apparatus of the initiation mechanism of the embodiment of FIG. 1, illustrating the needle cap or sheath after activation, and in the locked configuration.

Likewise, as shown in FIG. 6, once the aperture 34 of the protective cover 19 has passed the point or tip of the needle 7, the cap locking hatch 30 snaps from its oblique, angled position to a relatively perpendicular angle 40 with respect to the needle and inner walls of the protective cap 20 19, preventing access of the needle tip 7 through the aperture 34.

In fact, if the cap 19 were forced against the needle 6, the needle tip 7 would communicate with the needle tip notch 33, preventing the cap locking hatch 30 from bending to allow exposure of the tip.

Once in the locked position, the cap 19 is unalterably, redundantly locked about the needle 6, preventing accidental needle stick and contamination, or subsequent re-use by an addict or other individual.

Returning to FIG. 1, Locking initiation member 41 may be affixed or anchored to the syringe body 10 by a number of means currently known and used in the art, including adhesive, ultrasonic or thermal welding, mounting hardware such as banding or the like, or the housing 11 may simply be molded with said syringe body 10 as a single, injection molded piece.

Figure 7:
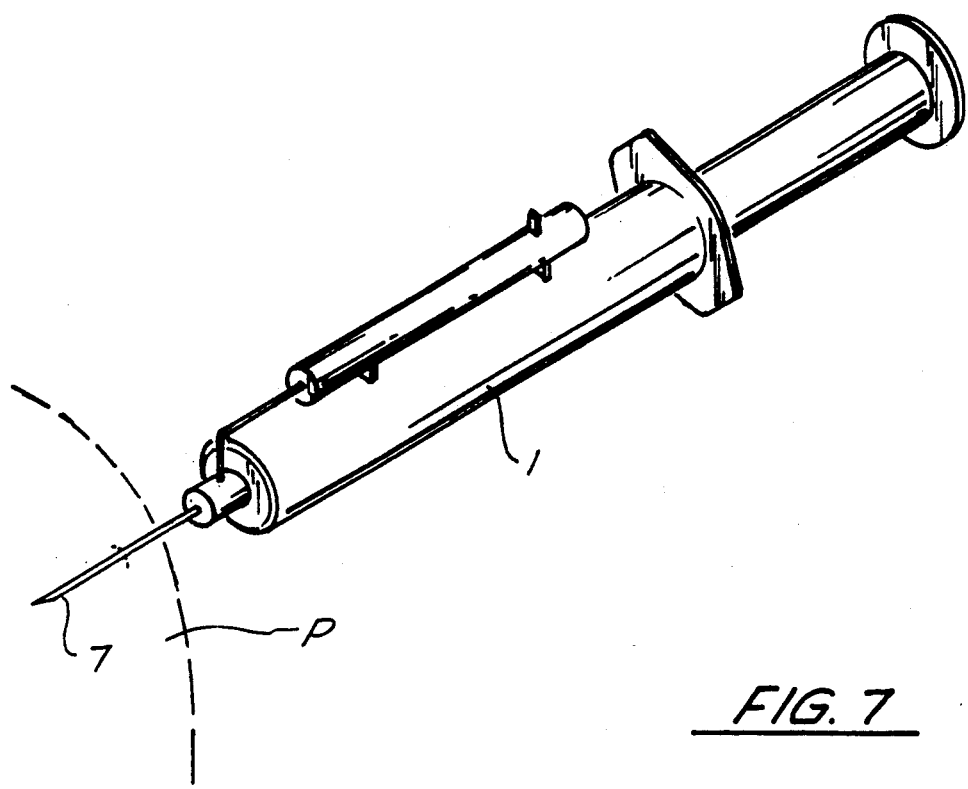
FIG. 7 is an isometric side view of the first step of utilizing the present invention, wherein the patient is injected with the needle.
Figure 8:
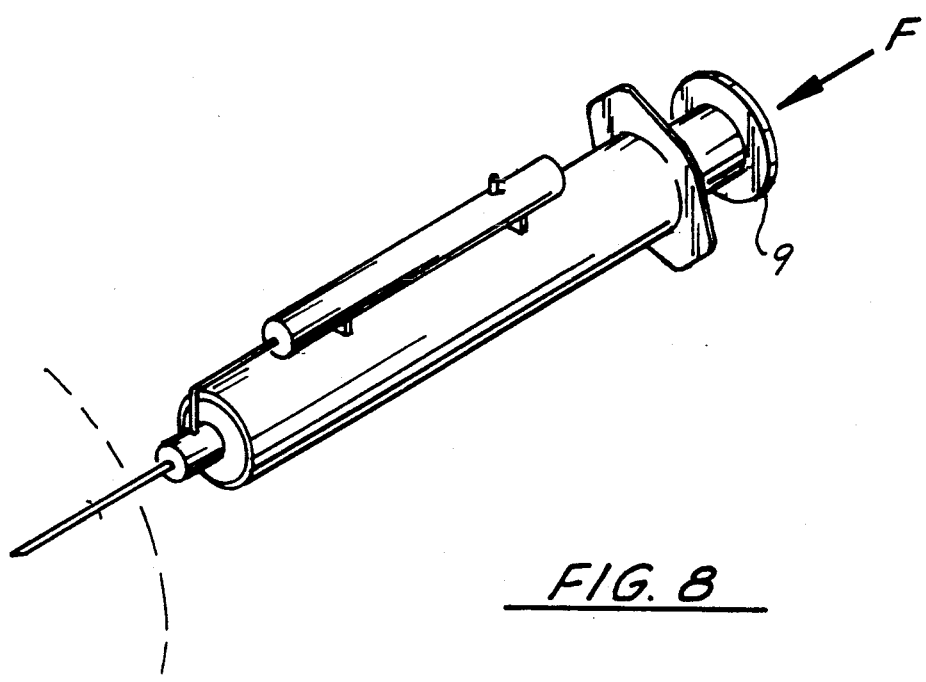
FIG. 8 is an isometric, side view of the second step of utilizing the present invention, wherein the plunger is initiated.

FIG. 7 illustrates the first step in utilizing the system of the present invention, wherein a patient P is injected with the needle 7 of the syringe 1, in the same manner as one would utilize a normal syringe. Likewise, as illustrated in FIG. 8, the syringe of the present invention has administered the contents of the syringe by applying force F to the plunger 9 of the syringe, in the direction of the needle.

Figure 9:
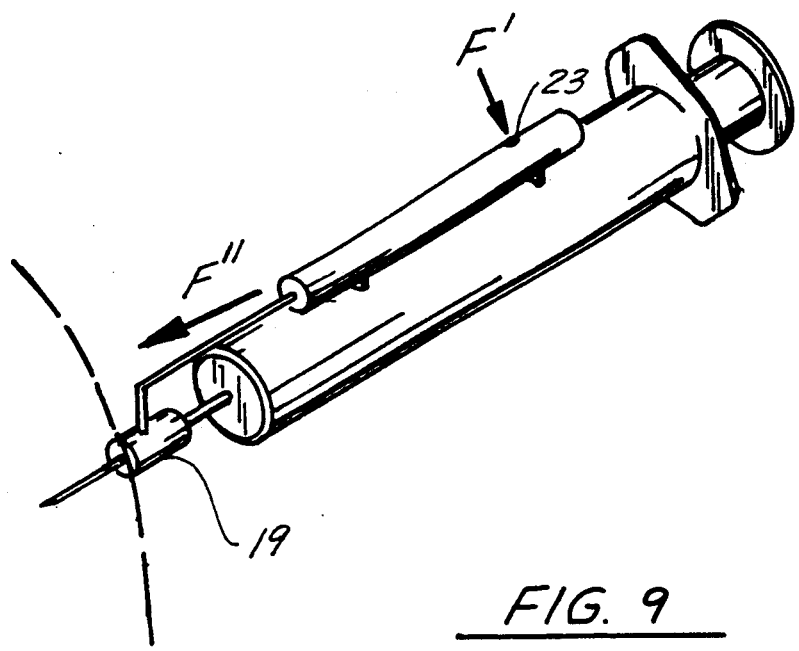
FIG. 9 is an isometric, side view of the third step of utilizing the present invention, wherein the pushbutton or activation tab is initiated, causing the needle cover housing to push forward along the needle towards the tip, contacting the skin of the patient.

FIG. 9 illustrates a means of utilizing the safety syringe of the present system in such a manner as to prevent exposure of the needle once it has been contaminated due to injection of the patient. As shown, while the needle is still in the patient, downward force F' is applied to the activation button or tab 23, allowing the spring in the housing to drive the protective cover 19 forward F'', such that the housing comes into contact with the skin of the patient, continuing to slide forward as the needle is being removed from the patient, until the protective cover completely covers the tip of the needle and locks into place, as shown in FIG. 4.

Figure 10:
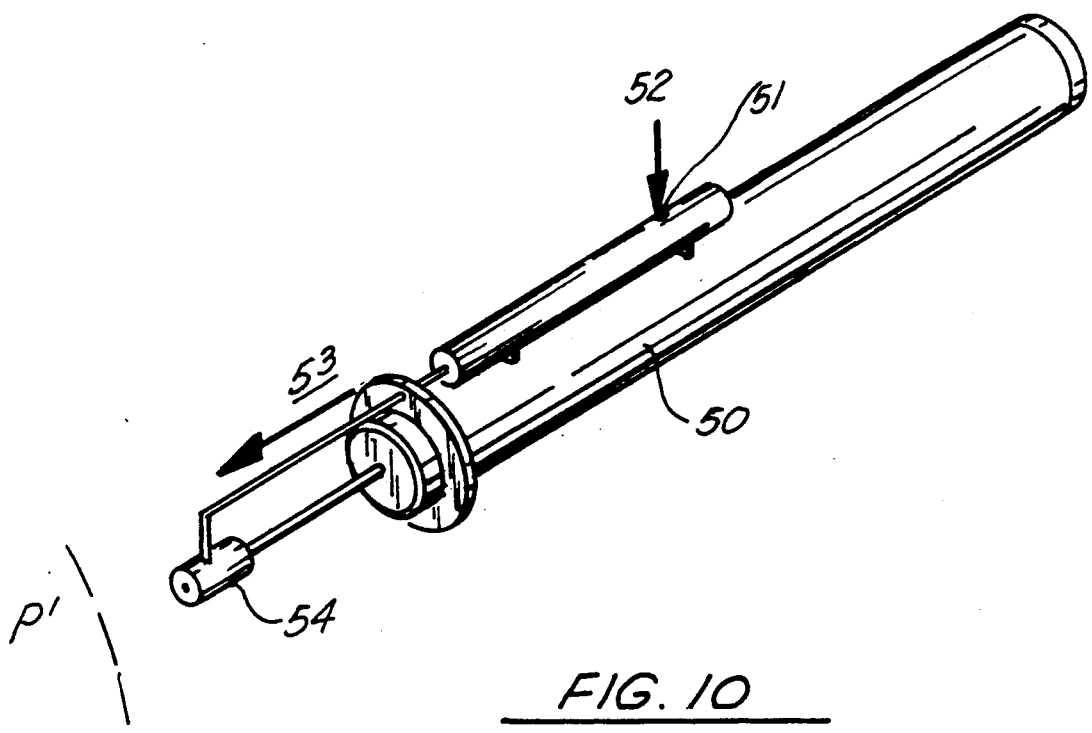
FIG. 10 is an isometric, side view of an alternative embodiment of the present invention, wherein an evacuation tube, IV Cannula, or the like utilizes the needle covering device of the present invention.
Figure 11:
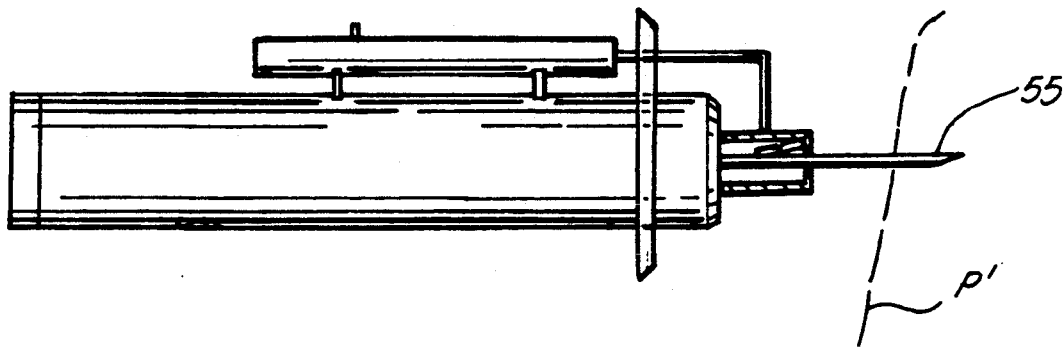
FIG. 11 is an isometric, side view of the alternative embodiment of FIG. 10, wherein the evacuation tube, IV Cannula, or the like is injected into a patient.
Figure 12:
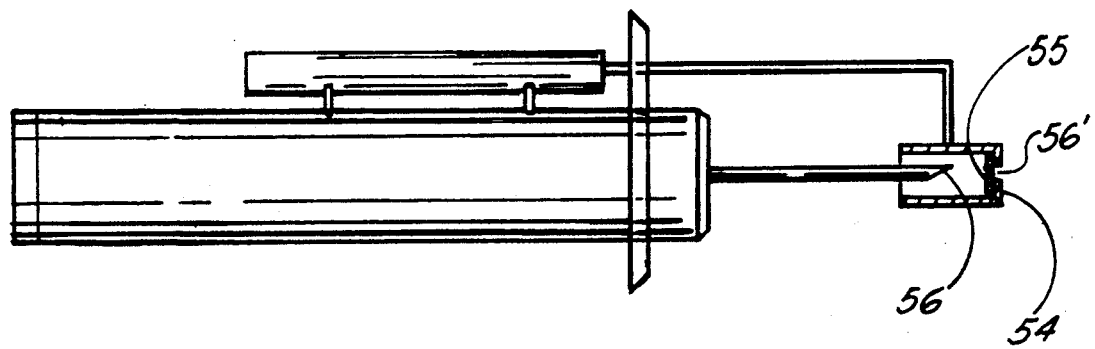
FIG. 12 is an isometric, side view of the alternative embodiment of FIG. 10, wherein the evacuation tube, IV Cannula, or the like's needle tip is covered via the needle cover.

FIGS. 10-12 illustrate an alternative embodiment of the safety syringe system of the present invention, wherein there is provided the same needle guard system for other, non-syringe needle systems, including IV cannulas, needled evacuation tubes, or like instruments. Containing the same components and operational characteristics as the syringe embodiment, the safety syringe system of the alternative embodiment contemplates a housing emanating from the barrel 50 of the instrument, an a needle protective cover resting about the base of the needle prior to instrument use, the system configured to drive the needle protective cover over the tip upon initiation of the activation button or tab.

As shown in FIG. 11, like the syringe system of the preferred embodiment, the present alternative embodiment's operation entails the injection of the needle tip 55 into the patient P'. Upon completion of the desired task, whether it be administration of fluid, removal of a blood sample, or like operation, the activation button or tab 51 is depressed 52 driving 53 the protective cover 54 about the needle tip as it is removed from the patient such that, as shown in FIG. 12, the needle tip 56 is enclosed in the protective cover 54, with the locking hatch 55 blocking the needle aperture 56 as with the preferred embodiment.

It is noted that the present system is not limited for use with a patient's body only, and can also be utilized when a needled instrument is used to administer or remove fluids from an IV via an artificial membrane or skin, or like operation. In such a use, the method of practicing the present invention is the same as discussed supra.

The apparatus of the present systems teach the pushbutton or initiation tab mounted along the side of the housing of the system; it is noted that the pushbutton or initiation tab need not be mounted to the side, and can, for example, be mounted at the end of the housing furthest from the needle; further, said pushbutton or initiation tab can comprise a variety of forms, including, for example, a sliding tab, break-away tab, etc.

The embodiment(s) described herein in detail for exemplary purposes, are of course subject of many different variations in structure, design, application, and methodology. Because many varying and different embodiments may be made within the scope of the inventive concept(s) herein detailed in accordance with the descriptive requirements of the law, it is to be understood that the details herein are to be interpreted as illustrative and not in a limiting sense.

I claim:

1. A safety system for preventing accidental needle stick or infection for use in conjunction with an instrument having a needle, comprising:

an instrument having a body comprising first and second ends, inner and outer walls, and a longitudinal axis, a needle having a base and tip, with the base of the needle being in communication with the second end of the body of the instrument;

a protective cover having inner and outer walls, and first and second ends having needle entrance and egress apertures, respectively, said protective cover being configured to longitudinally envelope the base of the needle in a storage position, and engage and cap the needle tip in an protected configuration after the instrument has been utilized;

biased activation means for urging said protective cover from the storage position to said unreusable configuration upon the pressing of a activation piece, said said biased activation means anchored to and longitudinally aligned with the body of the instrument, said biased activation means further comprising a housing having first and second ends;
   inner and outer walls forming a cavity therethrough;
   an aperture formed generally at or near said first end of said walls of said housing;
   a locking barrier formed about said inner walls generally near said second end;

said biased activation means further comprising a shaft having
   first and second ends;
   a body configured to communicate with said inner walls of said housing;
   a transversely configured activation piece, situated generally near said first end of said shaft, said activation piece configured to communicate with said aperture formed at or near said first end walls of said housing; and
   a locking member situated in proximity to said first end of said shaft, said locking member being configured to communicate with said locking barrier of said housing, locking said shaft in position once said locking member has passed through said locking barrier;
   bias means associated with said protective cover for urging said shaft in a direction longitudinally aligned with the needle, said bias means being initiated with the application of force on said activation piece of said shaft;
   communication means for connecting said shaft to said protective cover, said communication means transmitting said bias means from said shaft to said protective cover; and
   a cap locking hatch having first and second ends, said first end being configured to pliantly communicate with said protective cover in proximity to said second end, said cap locking hatch being configured to form a barrier juxtaposed to the needle tip and said egress aperture of said protective cover upon said needle tip being withdrawn into said protective cover.

2. The safety system of claim 1, wherein said cap locking hatch further comprises a needle tip notch configured to envelope the needle tip, should the needle tip come into contact with said cap locking hatch.

3. A safety system for preventing accidental needle stick or infection for use with an instrument having a needle, comprising:

an instrument having a cylindrical body comprising first and second ends, inner and outer walls, and a longitudinal axis, a needle having a base and tip, with the base of the needle being in communication with the second end of the body of the instrument;

a protective cover having inner and outer walls, and first and second ends having needle entrance and egress apertures, respectively, said protective cover being configured to longitudinally envelope the base of the needle in a storage position, and engage and cap the needle tip in an protected configuration after the instrument has been utilized;

activation means configured to urge said protective cover from said storage position to said un-reusable configuration upon the pressing of activation piece, said activation means being exterior to and longitudinally aligned with the body of the instrument, said activation means including
   a housing having first and second ends;
   inner and outer walls forming a cavity therethrough;
   an aperture formed at or generally near said first end of said walls of said housing;
   a locking barrier formed about said inner walls generally near said second
   said activation means further comprising a shaft having
   first and second ends;

a body configured to communicate with said inner walls of said housing;

an activation piece situated at or generally near said first end of said shaft, said activation piece being configured to communicate with said aperture formed at or generally near said first end of said walls of said housing; and a locking member situated in proximity to said first end of said shaft, said first and second locking members being configured to communicate with said locking barrier of said housing, said shaft in position once said locking member has passed through said locking barrier;

bias means associated with said protective cover for urging said shaft in a direction longitudinally aligned with the needle, said bias means being initiated with the application of downward force on said activation piece of said shaft;

communication means for connecting said shaft to said protective cover, said communication means transmitting said bias means from said shaft to said protective cover; and a cap locking hatch having first and second ends, said first end being configured to pliantly communicate with said protective cover in proximity to said second end, said cap locking hatch being configured to form a barrier juxtaposed to the needle tip and said egress aperture of said protective cover upon said needle tip being withdrawn into said protective cover.

4. An safety system for preventing accidental needle stick or infection for use in conjunction with an instrument having a needle, comprising:

an instrument having a cylindrical body comprising first and second ends, inner and outer walls, and a longitudinal axis, a needle having a base and tip, with the base of the needle being in communication with the second end of the body of the instrument;

a protective cover in longitudinal communication with said needle, said protective cover having inner and outer walls, and first and second ends having needle entrance and egress apertures, respectively, said protective cover being configured to longitudinally envelope the base of the needle in a storage position, and engage and cap the needle tip in a protected configuration after the instrument has been utilized;

bias means associated with said protective cover for urging said protective cover from said storage position to said unreusable configuration, urging said protective cover about the needle, toward the needle tip until said protective cover envelopes the needle tip; said bias means further comprising a shaft having first and second ends, said shaft longitudinally aligned with said instrument bias means for urging said shaft along a longitudinal path aligned with said instrument, generally toward said instrument tip, said bias means having first and second ends, said first end generally affixed to the cylindrical body of said instrument, said second end generally affixed to said shaft, lateral communication means for connecting said shaft to said protective cover, activation means for selectively initiating said bias means; and a cap locking hatch having first and second ends, said first end being configured to pliantly communicate with said protective cover in proximity to said second end of said protective cover, said cap locking hatch being configured to form a barrier juxtaposed to the needle tip and said egress aperture of said protective cover upon said needle tip being withdrawn into said protective cover.

5. A method of preventing accidental infection, comprising the following steps:

(a) providing a safety system in conjunction with an instrument having a needle, comprising an instrument having a cylindrical body comprising first and second ends, inner and outer walls, and a longitudinal axis, a needle having a base and tip, with the base of the needle being in communication with the second end of the body of the instrument;

a protective cover in longitudinal communication with said needle, said protective cover having inner and outer walls, and first and second ends having needle entrance and egress apertures, respectively, said protective cover being configured to longitudinally envelope the base of the needle in a storage position, and engage and cap the needle tip in a protected configuration after the instrument has been utilized;

bias means associated with said protective cover for urging said protective cover from said storage position to said unreusable configuration, urging said protective cover about the needle, toward the needle tip until said protective cover envelopes the needle tip; said bias means further comprising a shaft having first and second ends, said shaft longitudinally aligned with said instrument;

means for urging said shaft along a longitudinal path aligned with said instrument, generally toward said instrument tip, said bias means having first and second ends, said first end generally affixed to the cylindrical body of said instrument, said second end generally affixed to said shaft, lateral communication means for connecting said shaft to said protective cover, activation means for selectively initiating said bias means; and a cap locking hatch having first and second ends, said first end being configured to pliantly communicate with said protective cover in proximity to said second end, said cap locking hatch being configured to form a barrier juxtaposed to the needle tip and said egress aperture of said protective cover upon said needle tip being withdrawn into said protective cover, b. inserting said needle into a membrane, skin, or body of a patient; and c. protecting said needle, and lessening the possibility of infection by needle prick from said instrument after use, including the following steps i. applying force to said activation means, ii. selectively initiating said bias means, urging said shaft in a direction longitudinally aligned with said needle, iii. transmitting said bias means from said shaft to said protective cover via said communication means, iv. slidingly motivating said protective cover from said storage position about the base of said needle towards said needle tip until said protective cover envelopes said needle tip, withdrawing said needle tip from said needle aperture, v. blocking said needle aperture via said cap locking hatch.

6. The method of claim 5, wherein there is included in step "a" the additional step of providing a needle tip notch to said cap locking hatch, said needle tip notch configured to envelope the needle tip should the needle tip come into contact with said cap locking hatch.

7. The method of claim 6, wherein there is further included the step of aligning said needle tip notch of said cap locking hatch in the longitudinal axis of the needle, so that the needle tip notch communicates with the needle tip upon the application of pressure against said protective cover, toward said needle base.

8. A method of preventing accidental infection, comprising the following steps:

(a) providing a safety system in conjunction with an instrument having a needle, comprising an instrument having a cylindrical body comprising first and second ends, inner and outer walls, and a longitudinal axis, a needle having a base and tip, and a length situated fully along the longitudinal axis of the body of said instrument, with the base of the needle being in communication with the second end of the body of the instrument;

a protective cover in longitudinal communication with said needle, said protective cover having inner and outer walls, and first and second ends having needle entrance and egress apertures, respectively, said protective cover being configured to longitudinally envelope the base of the needle in a storage position, and engage and cap the needle tip in a protected configuration after the instrument has been utilized;

bias means associated with said protective cover for urging said protective cover from said storage position to said unreusable configuration, urging said protective cover about the needle, toward the needle tip until said protective cover envelopes the needle tip; said bias means further comprising a shaft having first and second ends, said shaft longitudinally aligned with said instrument;

means for urging said shaft along a longitudinal shaft path aligned with said instrument, generally toward said instrument tip, said bias means having first and second ends, said first end generally affixed to the cylindrical body of said instrument, said second end generally affixed to said shaft, lateral communication means for connecting said shaft to said protective cover, activation means for selectively initiating said bias means; and a cap locking hatch having first and second ends, said first end being configured to pliantly communicate with said protective cover in proximity to said second end, said cap locking hatch being configured to form a barrier juxtaposed to the needle tip and said egress aperture of said protective cover upon said needle tip being withdrawn into said protective cover.

b. introducing said needle of said instrument into a membrane, skin, or patient's body;

c. prior to removing said needle from the membrane, skin, or patient's body, in order to protect said needle once it has been removed from the membrane, skin, or patient's body, and lessening the possibility of infection by needle prick from said instrument after use, the present method further includes the following steps i. applying force on said activation means, ii. selectively initiating said bias means, urging said shaft in a direction longitudinally aligned with said needle, iii. transmitting said bias means from said shaft to said protective cover via said communication means, iv. slidingly motivating said protective cover from said storage position about the base of said needle towards said needle tip until said protective cover communicates with the outer skin of the membrane, skin, or patient;

v. removing said needle from the membrane, skin, or patient's body, while simultaneously allowing said bias means to further slidingly motivate said protective cover about said needle towards said needle tip as said needle is being removed from the membrane, skin, or patient, until the needle is completely removed and said protective cover simultaneously envelopes said needle tip upon removal, withdrawing said needle tip from said needle aperture, containing said needle and thereby preventing infection via needle prick with said needle.

9. The method of claim 8, wherein there is further included as step "VI" the step of blocking said needle aperture via said cap locking hatch.

* * * * *